United States Patent [19]

DeMeyts

[11] Patent Number: 5,227,466
[45] Date of Patent: Jul. 13, 1993

[54] INSULIN RECEPTOR BINDING SITE
[75] Inventor: Pierre DeMeyts, Pasadena, Calif.
[73] Assignee: City of Hope, Duarte, Calif.
[21] Appl. No.: 213,918
[22] Filed: Jun. 30, 1988
[51] Int. Cl.⁵ .................... A61K 37/02; C07K 5/00
[52] U.S. Cl. ................................. 530/305; 530/303
[58] Field of Search ........................ 530/305, 303

[56] References Cited
U.S. PATENT DOCUMENTS
4,761,371 8/1988 Bell et al. ............................ 530/326

FOREIGN PATENT DOCUMENTS
0286147 4/1988 European Pat. Off. .

OTHER PUBLICATIONS
Knutson, "Insulin-Binding Peptide Design and Characterization" *Journal of Biological Chemistry* 263:14146–14151 (1988).
Ebina et al., *Cell* 40:747–758 (1985).
Ullrich, et al., *Nature* 313:756–761 (1985).
Ullrich, et al., *The Embo J.* 5:2503–2512 (1986).
Jan. 29, 1988, HHS Grant Application; cover page; p. 2; Table of Contents, p. 3; Biographical Sketch, pp. 10–12; Background, pp. 37–44; "Literature", pp. 67–69.
Application for Diabetes Research Grant, Feb. 1, 1988, cover page, pp. 9–18, and References, pp. 35–37.

*Primary Examiner*—Johann Richter
*Attorney, Agent, or Firm*—Edward S. Irons

[57] ABSTRACT

Amino acid residue sequence and ternary structure of receptor domains for insulin and IGF-I molecules.

8 Claims, 8 Drawing Sheets

FIG.2

\* Invariant or mostly invariant insulin residues

| INSULIN/RECEPTOR | 19 | 20 | 21 | 22 | 23 | 24 | 25 | -- | 26 | 27 | 28 | 29 | 30 | | Last Residue Number |
|---|---|---|---|---|---|---|---|---|---|---|---|---|---|---|---|
| B | * | * | * | * | * | * | * | | * | * | * | * | * | | |
| INSULIN 831 | CYS | GLY | GLU | ARG | GLY | PHE | PHE | ASN | TYR | THR | PRO | LYS | THR | | |
| 226 | ARG | GLY | SER | ARG | LEU | PHE | PHE | LEU | TYR | ALA | LEU | VAL | ILE | PHE | 98 |
| 239 | VAL | ALA | CYS | ARG | ASN | PHE | TYR | HIS | ASP | GLY | ASP | CYS | VAL | GLU | 241 |
| 376 | GLY | CYS | PRO | PRO | PRO | TYR | TYR | ARG | PHE | GLN | ARG | TRP | ARG | CYS | 254 |
| 395 | LEU | VAL | SER | LEU | SER | PHE | PHE | ALA | LYS | LEU | ASP | LEU | ILE | ARG | 390 |
| 422 | ILE | GLY | ASN | TYR | SER | PHE | TYR | HIS | LEU | ASP | ARG | GLN | ASN | LEU | 410 |
| 501 | THR | GLN | GLY | LYS | LEU | PHE | PHE | HIS | TYR | ASN | ASN | LYS | LEU | CYS | 436 |
| | LEU | GLY | PHE | MET | LEU | PHE | TYR | LYS | GLU | ALA | PRO | TYR | GLN | ASN | 515 |

First Residue Number (Ullrich's Numbering)

---

1 Synthetic peptide 86-103 binds insulin

|   | B | 19 | 20 | 21 | 22 | 23 | 24 | 25 | 26 | 27 | 28 | 29 | 30 |
|---|---|---|---|---|---|---|---|---|---|---|---|---|---|
|   |   |   |   |   | \|—COOPERATIVE SITE—\| | | | | | | | |
| INSULIN |   | CYS | GLY | GLU | ARG | GLY | PHE | PHE | – – | TYR | THR | PRO | LYS | THR |
| INS. REC. |   | ARG | GLY | SER | ARG | GLY | LEU | PHE | – – | TYR | ALA | LEU | VAL | ILE |
| IGFI REC. |   | ARG | GLY | TRP | LYS | LEU | PHE | TYR | – – | TYR | ALA | LEU | VAL | ILE |
| IGFI |   | CYS | GLY | ASP | ARG | GLY | PHE | TYR | ASN | PHE | – – | – – | LYS | PRO |
| EGF REC. |   | ARG | GLY | ASN | MET | TYR | TYR | GLU | ASN | SER | TYR | ALA | LEU | VAL | ILE |

FIG. 5

INSULIN RECEPTOR BINDING SITE

This invention relates to the locus of a domain on the α subunit of the insulin receptor which is involved in the binding of the insulin molecule, and to a homologous domain of the insulin-like growth factor I (IGF-I) receptor involved in binding IGF-I. More particularly the invention relates to natural and synthetic fragments of such domains and to amino acid residue sequences thereof which are involved in binding the active site of the insulin or IGF-I molecule. The invention also relates to physical and graphic representations of such fragments and sequences and to the use of such fragments and sequences and such physical and graphic representations including computer generated graphic representations as templates and in other ways to design, for example, insulinomimetic drugs.

BACKGROUND cDNA of both the insulin and the IGF-I receptor have been cloned and sequenced by two groups and successful expression in mammalian cells of biologically active receptors was readily achieved.[1] The receptors are glycoproteins which consist of a heterotetramer of two extracellular α subunits and two transmembrane β subunits which have both an extracellular and an intracellular portion. The α subunits contain the insulin binding site. It is plausible that each α subunit may contain one binding site. The insulin receptor has homology with the insulin-like growth factor I (IGF I) receptor and with the epidermal growth factor receptor, the human c-erb-2 oncogene, and the v-ros oncogene-encoded tyrosine kinase.

[1] Ebina, et al. (1985) Cell 46:747-758; Ullrich, et al. Nature 313:756-761 (1985); Ullrich, et al., The Embo J. 5:2503-2512 (1986). Ebina and Ullrich utilize different sequence numbers. The Ullrich sequence numbers are used exclusively herein.

Knowledge of receptor structures is limited to the primary sequence deduced from cDNA cloning. This information has produced few clues as to the precise localization of the insulin or IGF-I binding domain on the α subunits, each of which contains more than 700 amino acid residues. Nor is definitive information of the secondary or tertiary structure of the receptors available.

SUMMARY OF THE INVENTION

This invention entails identification of receptor domains involved in the binding of insulin or IGF-I molecules, the amino acid residue sequences of such domains, and their secondary and tertiary structure. The invention includes natural and synthetic fragments of such domains and sequences which are effective in implementation of the binding and recognition of the insulin or IGF-I molecule by the receptors, as well as physical and graphic representations of these domains. The use of such fragments and templates derived therefrom to design, for example, insulinomimetic drugs is an objective of the invention.

DETAILED DESCRIPTION OF THE DRAWINGS

FIG. 2 illustrates the homology of various receptor fragments containing at least two aromatic side-chains with the C-terminal end of insulin B-chain.

FIG. 5 depicts homology between C-terminal ends of insulin and IGF-I B-Chains and receptors for insulin, IGF-I and EGF.

Identification of the Insulin Receptor Binding Domain

Figure 3:
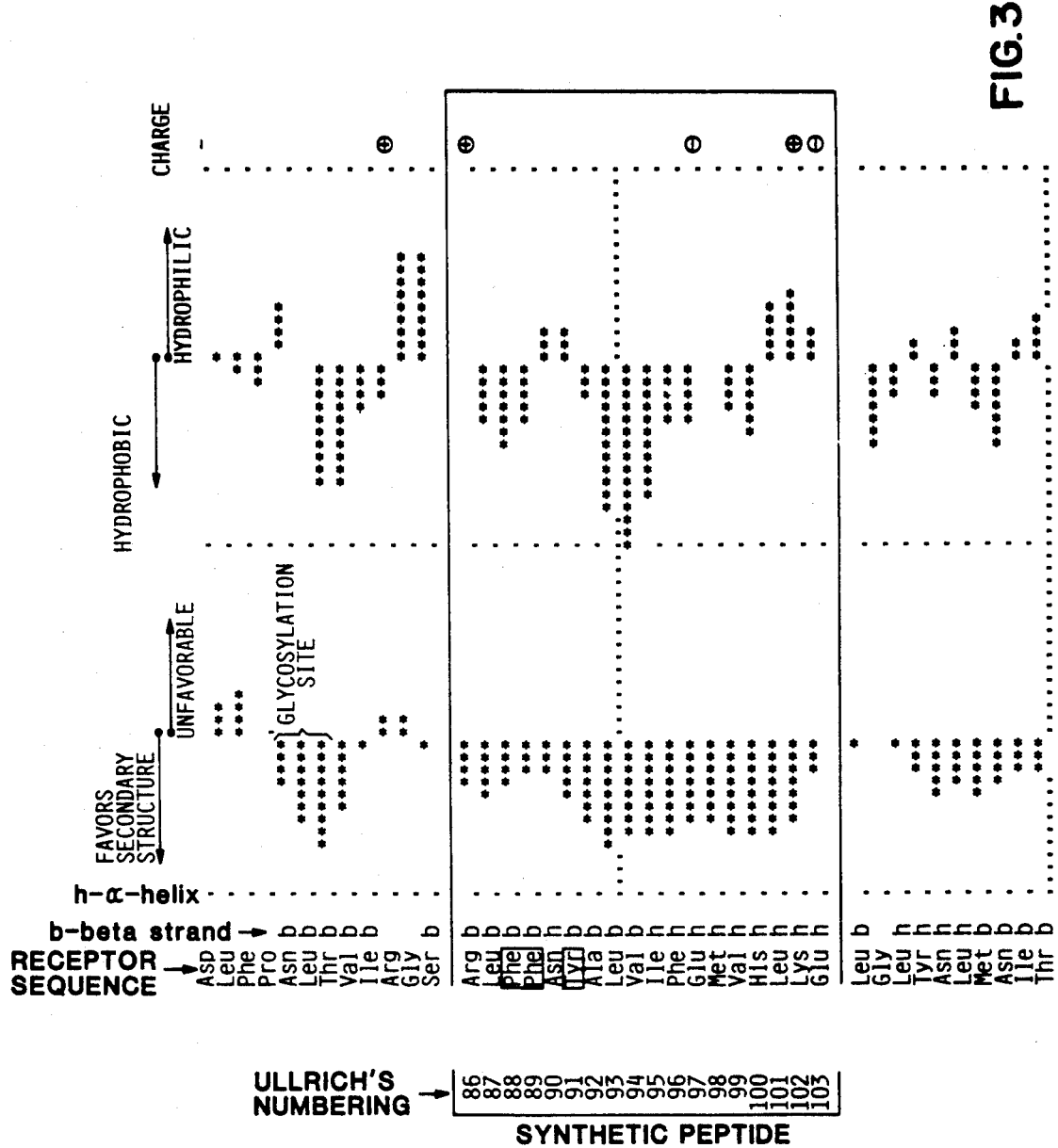
FIG. 3 depicts a computer prediction of the α subunit secondary structure and hydropathy profile of the insulin α subunit.

The insulin molecule B-chain residues $B_{23-26}$ Gly-Phe-Phe-Tyr are involved directly in a receptor binding domain. It is also known that the C-terminal portions of the monomeric insulin B-chains bind inter se to form the insulin dimer. From a study of the dimer interface (see FIG. 1A), it may be deduced that a receptor sequence for interaction in a similar fashion with the same C-terminal portion of the insulin monomer would (i) contain two or three Phe or Tyr chains; and (ii) may have some homology with the C-terminal end of the insulin B-chain;

(iii) be in a hydrophobic environment;

(iv) be in a β-sheet secondary structure;

Inspection of the known sequence of the receptor α subunit reveals various stretches containing at least two or three Phe or Tyr chains in close proximity. Of these, the 88-91 (Phe-Phe-Asn-Tyr) stretch was selected because:

(i) sequence 84 to 91 has 5 residues homologous to the invariant or mostly invariant insulin residues 20-26. See FIG. 2;

(ii) a computer-generated secondary structure and hydropathy profile of the α subunit indicates that the receptor segment 78-94 containing the Phe-Phe-Asn-Tyr to be a β-sheet followed by a helical portion 95 to 103 the whole sequence being largely hydrophobic. See FIG. 3.

A synthetic 18 amino acid peptide corresponding to the receptor sequence 86-103 was synthesized on a solid support utilizing the p-alkoxybenzyl ester anchoring linkage of Wang.[2] The amino acids were amino-protected by the N-fluorneylmethoxycarbonylamino (Fmoc) group. The side chains were protected with t-butyl or other appropriate protecting groups. After synthesis the peptide was cleaved from the solid support by trifluoroacetic acid containing suitable solvents and other reagents to protect the peptide during this cleavage. The peptide was then passed through a Sephadex-G-10 and final purification is achieved by using a C-18 column on an HPLC system. The exact molecular weight of the peptide was verified on a high resolution mass spectrometer. It was found to be highly hydrophobic as evidenced by substantial insolubility in less than 90% dimethylsulfoxide (DMSO). In water at high concentrations the peptide formed a gel like suspension and eventually precipitated as transparent crystalline-appearing structures.

[2] Wang, S.S., *J. Am. Chem. Soc.* 95:1328-1333 (1973).

The amino acid residues in this peptide are in the sequence depicted by the following Sequence I:

ARG—LEU—PHE—PHE—ASN—TYR—ALA—LEU—
86   87   88   89   90   91   92   93

VAL—ILE—PHE—GLU—MET—VAL—HIS—LEU—
94   95   96   97   98   99   100   101

LYS—GLU
102   103

Figure 4:
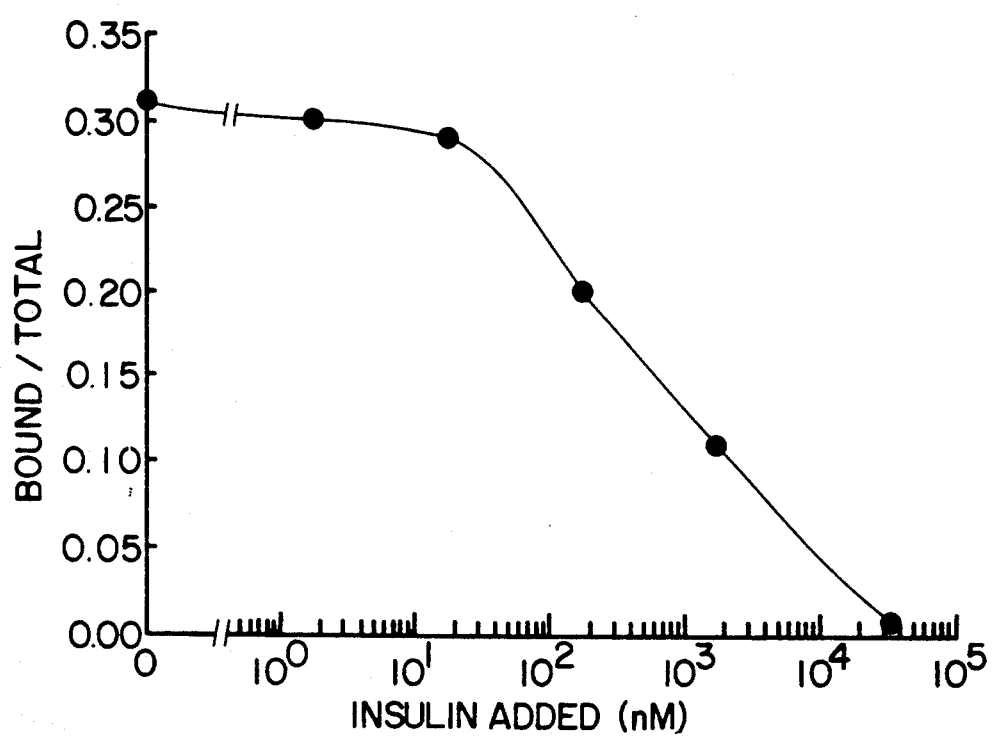
FIG. 4 is an insulin competition curve with a synthetic receptor peptide.

To test for insulin binding, a water suspension of the peptide was incubated at room temperature with a tracer of $^{125}$I-insulin followed by simple centrifugation. The peptide was found to bind up to 30% of the tracer. The binding was displacable by an excess of unlabelled insulin. See FIG. 4. The apparent dissociation constant was $\sim 6 \times 10^{-7}$M. Non-specific binding was negligible. The peptide also bound $^{125}$I-IGF I, but less well, while $^{125}$I-EGF (epidermal growth factor) and $^{125}$I-hGH (human growth hormone) showed no specific binding. These data correspond well to the predictions from sequence homologies in FIG. 5.

This invention includes modifications of Sequence I to which additional residues corresponding to preceding and succeeding portions of the receptor $\alpha$ subunit are present. For example, the invention includes a Sequence II which also includes residues 83 to 85 of the insulin receptor $\alpha$ subunit as follows:

ARG—GLY—SER—ARG—LEU—PHE—PHE—ASN—
83   84   85   86   87   88   89   90

TYR—ALA—LEU—VAL—ILE—PHE—GLU—MET—
91   92   93   94   95   96   97   98

VAL—HIS—LEU—LYS—GLU
99   100   101   102   103

The invention also includes modification of Sequence I in which one or more additional residues are added at one or both ends of the sequence to increase solubility. Specifically, the invention contemplates a Sequence III which includes (LYS)$_x$—ARG—LEU—PHE—PHE—ASN—TYR—ALA—
86   87   88   89   90   91   92

LEU—VAL—ILE—PHE—GLU—MET—VAL—HIS—
93   94   95   96   97   98   99   100

LEU—LYS—GLU—(LYS)$_y$
101   102   103 in which x and y are each 0, 1 or 2 with the provision that at least x or y is 1.

The invention further includes Sequences I and II coupled to beads of polystyrene or other solid supports for use in solid phase assays and to keyhole limpet hemocyanin for use in the production of antibodies to said sequences.

The invention also includes the synthesis of an oligonucleotide corresponding to the Sequence I peptide and its expression in *E. coli* as part of a fusion protein with, for example, $\beta$-galactosidase, dihydrofolate reductase, or a synthetic IgG-binding domain from staphylococcus aureus protein A,[3] in order to produce a fusion protein containing the peptide in order to generate antibodies to said sequence or in order to perform physical studies such as x-ray crystallography.

[3] Lowenalder, B., et al. *Gene* 58:87-97 (1987).

Figure 1B:
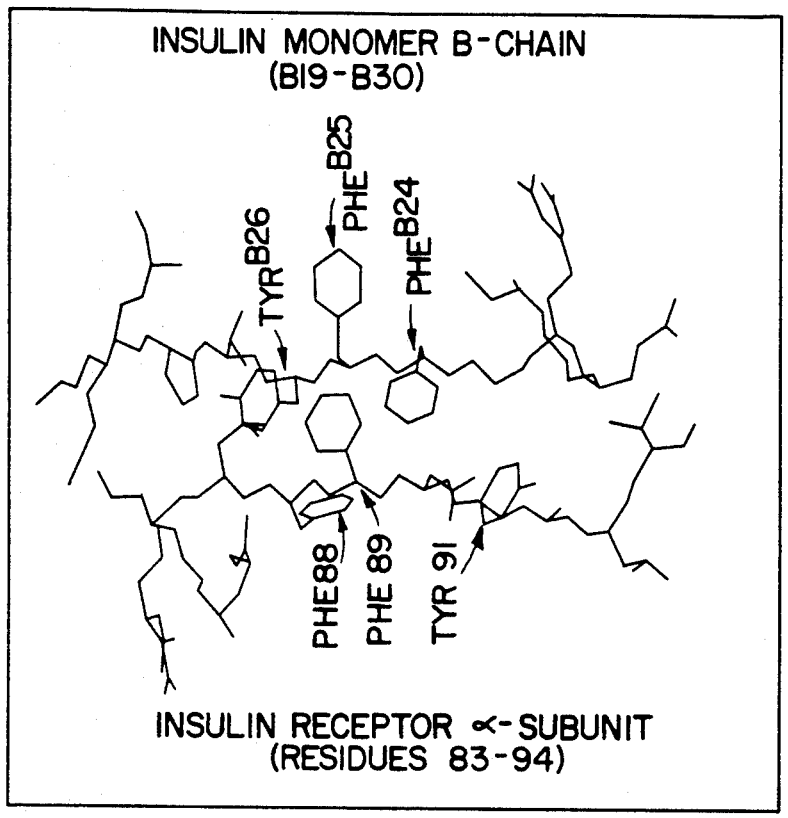
FIG. 1B show a molecular graphic model of the insulin sequence B19-B30 of one insulin monomer in the dimer interface replaced by sequence 83-94 of the insulin receptor.
Figure 1A:
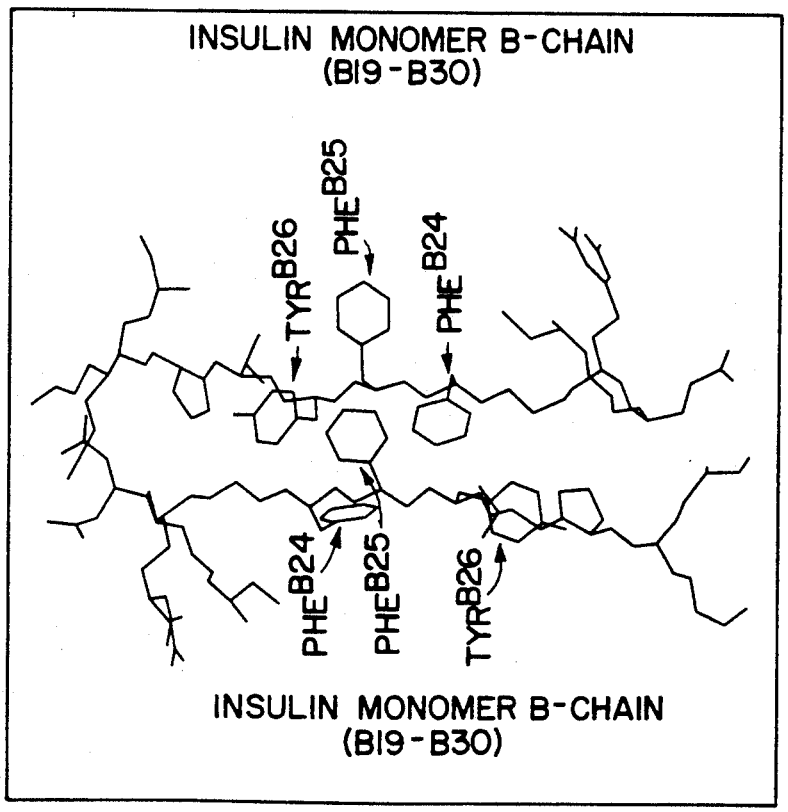
FIG. 1A depicts the insulin dimer interface.

FIG. 1B is a computer generated graphic model that illustrates replacement of the side chains of residues CYS$^{B19}$, GLU$^{B21}$, GLY$^{B23}$ and B26-30 of one of the insulin monomers shown in FIG. 1A by the side chains of the residues occupying homologous positions in the insulin receptor sequence--specifically by ARG 83, SER 85, LEU 87 and ASN-TYR-ALA-LEU-VAL. Thus FIG. 1B shows a molecular graphic model of the insulin sequence B19-B30 of one insulin monomer in the dimer interface replaced by sequence 83-94 of the insulin receptor. The similarity to the insulin dimer interface, FIG. 1A, is striking.

This data indicates that residues 83 to 94 of the insulin receptor $\alpha$ subunit includes at least an effective portion of a domain involved in binding the active site of the insulin molecule.

Figure 6C:
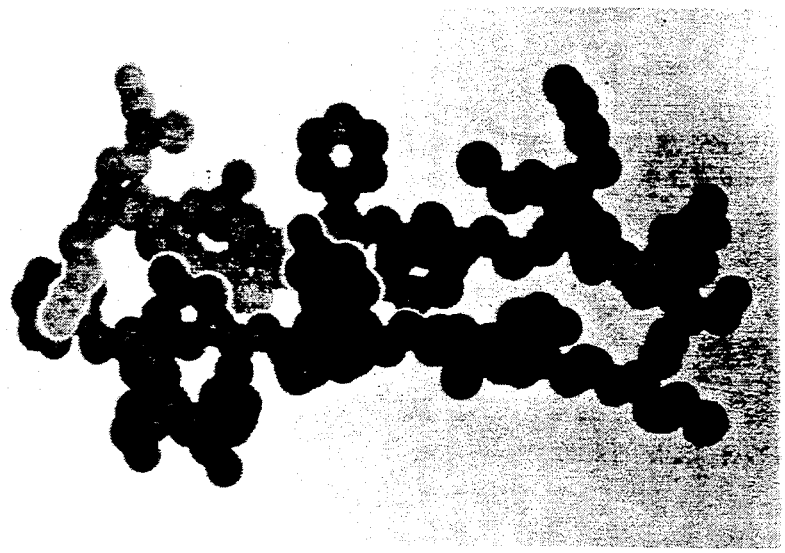
FIG. 6C is a graphic representation of the IGF-I receptor domain-insulin pair.
Figure 6B:
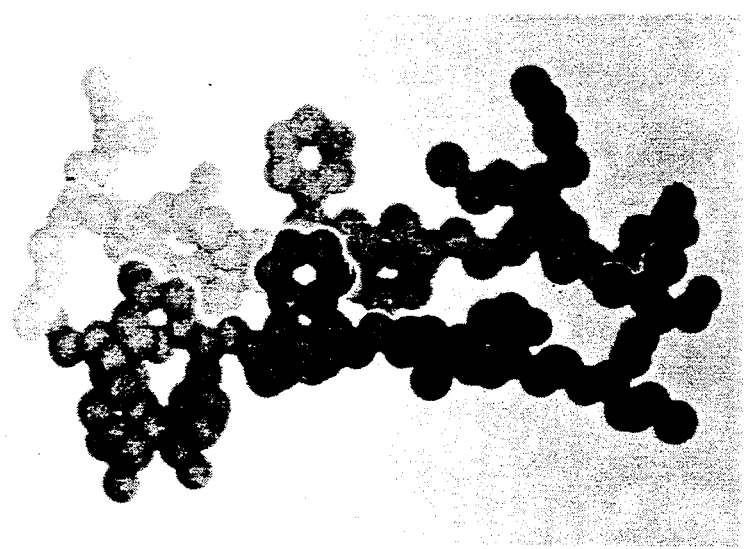
FIGS. 6A and 6B are graphic representations of the insulin-insulin dimer pair and the insulin-insulin receptor domain including the residues 83-94.
Figure 6A:
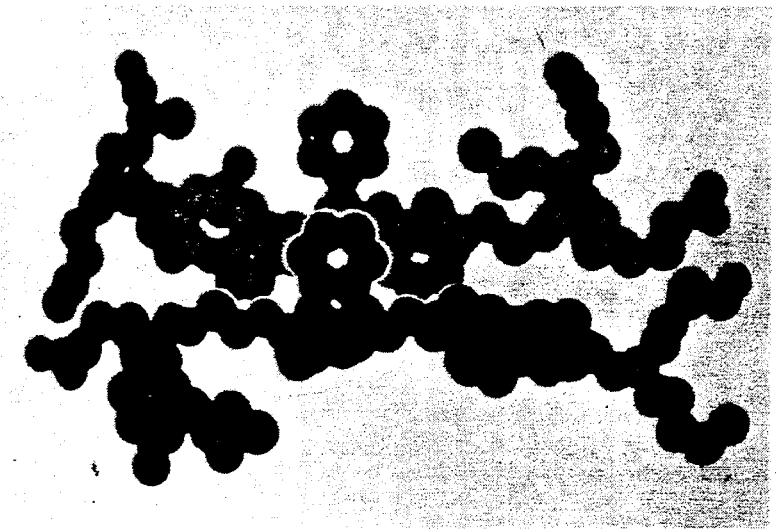
Figure 7A:
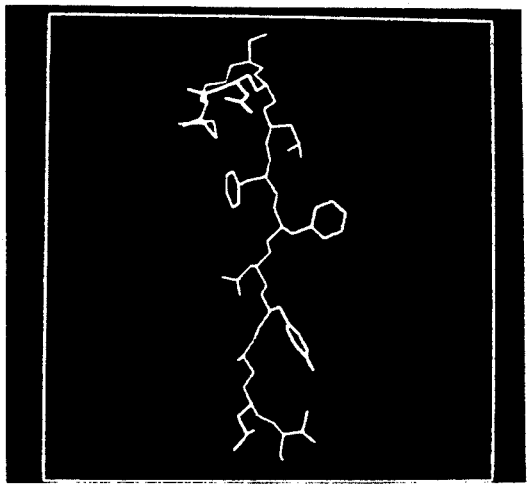
FIGS. 7A to 7D are computer generated graphic models of the insulin receptor α subunit including the residues 83-94 from four different angles.
Figure 7B:
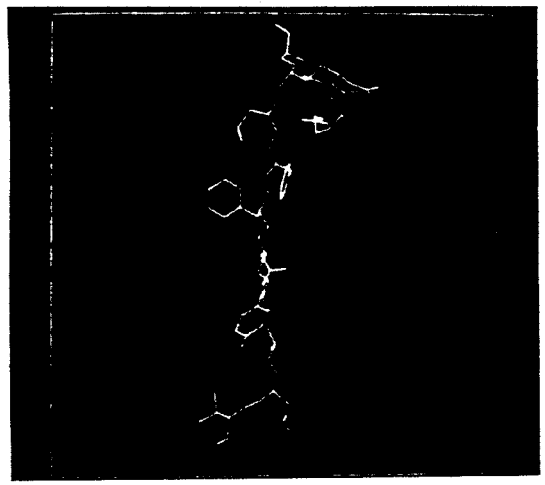
Figure 7C:
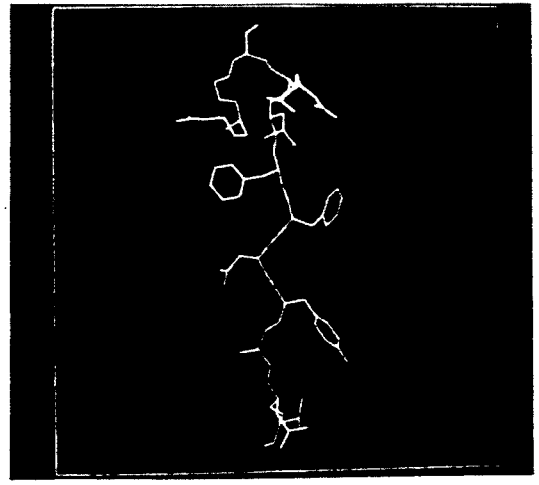
Figure 7D:
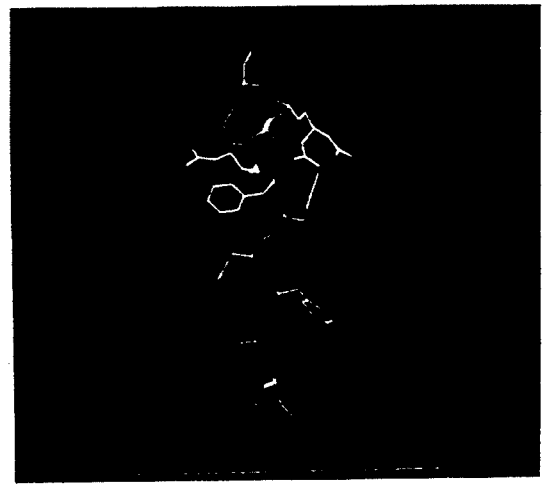
Figure 8A:
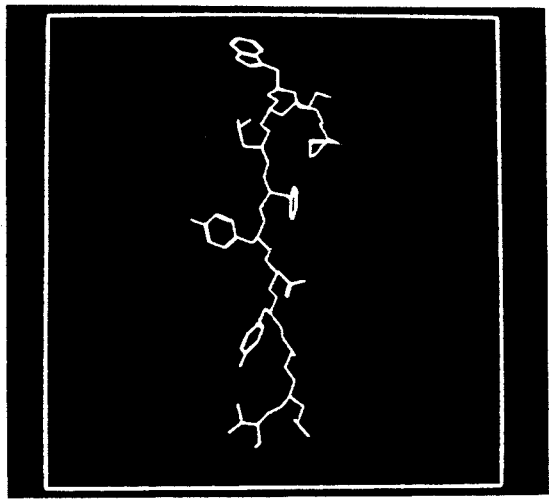
FIGS. 8A to 8D are graphic representations of the IGF-I receptor domain including the residues 77-97 from four different angles.
Figure 8B:
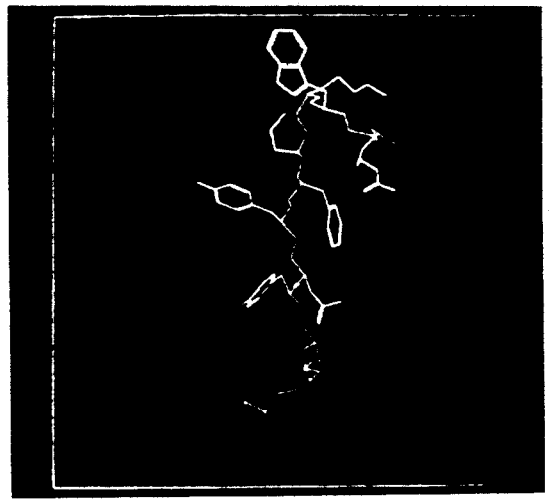
Figure 8C:
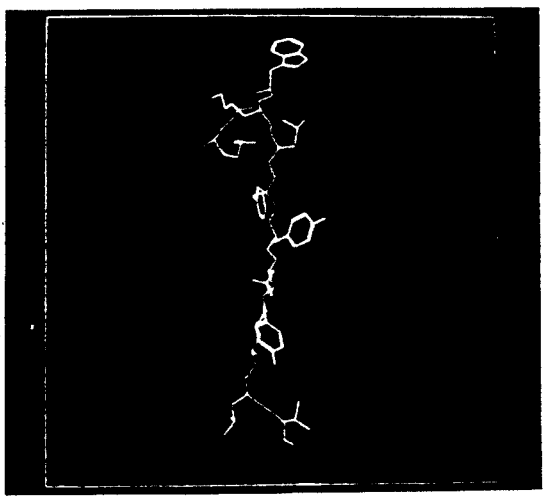
Figure 8D:
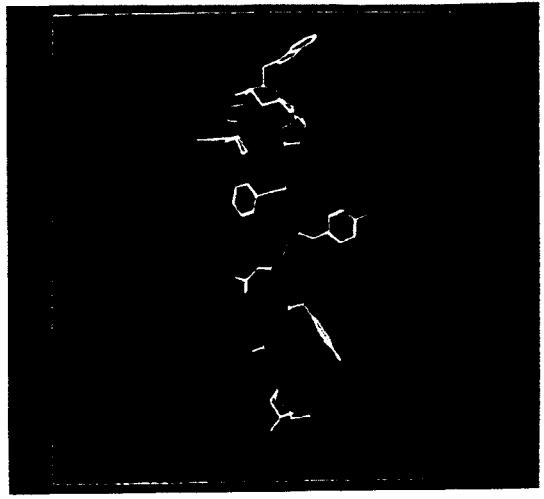

FIGS. 6A and 6B are graphic representations of the insulin-insulin dimer pair and of the insulin-insulin receptor domain including the residues 83-94. FIG. 6C is a graphic representation of the IGF-I receptor domain-insulin pair.

FIGS. 7A-D are computer generated graphic models of the insulin receptor $\alpha$ subunit including the residues 83-94 from four different angles.

FIGS. 8A-D are graphic representations of the IGF-I receptor domain, including the residues 77-97 from four different angles.

IDENTIFICATION OF THE IGF-I RECEPTOR BINDING DOMAIN

The involvement of Sequence IV of the IGF-I receptor residues 77-97 homologous to insulin receptor sequence 83-103 in IGF-I binding is evidenced by the following:

(i) insulin and IGF-I bind to each other's receptors;

(ii) sequence B$^{23-26}$ of the insulin molecule is conserved in IGF-I molecule (GLY-PHE-TYR-PHE instead of GLY-PHE-PHE-TYR);

(iii) sequence 83-97 of insulin receptor is highly conserved in IGF-I receptor;

(iv) synthetic peptide (Sequence I) binds IGF-I;

(v) a computer generated graphic model that illustrates replacement of the side chains of residues CYS$^{B19}$, GLU$^{B21}$, GLY$^{B23}$ and B$^{26-30}$ of one of the insulin monomers shown in FIG. 1A by the side chains of the residues occupying homologous positions in the IGF-I receptor sequence--specifically by ARG, TRP, LYS, LEU, and ASN-TYR-ALA-LEU-VAL, also shows striking similarity to the insulin dimer interface (FIG. 6C).

Accordingly, the invention also includes the following Sequence IV of the IGF-I receptor:

ARG—GLY—TRP—LYS—LEU—PHE—TYR—ASN—
77   78   79   80   81   82   83   84

TYR—ALA—LEU—VAL—ILE—PHE—GLU—MET—
85   86   87   88   89   90   91   92

THR—ASN—LEU—LYS—ASP
93   94   95   96   97

The invention further comprises physical and graphic representations of Sequence IV and the use thereof in the design of drugs.

I claim:

1. A purified natural or a synthetic peptide which consists essentially of at least a portion of Sequence I or Sequence II or Sequence III which binds the human insulin molecule.

2. A purified natural amino acid residue sequence which consists essentially of Sequence I.

3. A purified natural amino acid residue sequence which consists essentially of Sequence II.

4. A synthetic peptide which consists essentially of amino acid residue Sequence I, or amino acid residue Sequence II, or amino acid residue Sequence III.

5. A purified or a synthetic fragment of the human insulin receptor α subunit which consists essentially of at least so much of Sequence I as is effective to bind the human insulin molecule, said fragment having a ternary structure as depicted by any of FIGS. 7A, 7B, 7C or 7D.

6. An isolated fragment of the amino acid sequence of the human insulin receptor α subunit, said fragment consisting essentially of an insulin binding site or an insulin-like growth factor I binding site.

7. A non-naturally occurring peptide consisting essentially of an amino acid residue sequence selected from the group consisting of

ARG—GLY—SER—ARG—LEU—PHE—PHE—ASN—
 83    84    85    86    87    88    89    90

TYR—ALA—LEU—VAL—ILE—PHE—GLU—MET—
 91    92    93    94    95    96    97    98

VAL—HIS—LEU—LYS—GLU,
     99   100   101   102   103

(LYS)$_x$—ARG—LEU—PHE—PHE—ASN—TYR—ALA—
       86    87    88    89    90    91    92

-continued
LEU—VAL—ILE—PHE—GLU—MET—VAL—HIS—
 93    94    95    96    97    98    99   100

LEU—LYS—GLU—(LYS)$_y$,
     101   102   103

LYS—ARG—GLY—SER—ARG—LEU—PHE—PHE—
 83    84    85    86    87    88    89

ASN—TYR—ALA—LEU—VAL—ILE—PHE—GLU—
 90    91    92    93    94    95    96    97

MET—VAL—HIS—LEU—LYS—LYS,
     98    99   100   101   102

LYS—ARG—GLY—SER—ARG—LEU—LEU—PHE—
 83    84    85    86    87    88    89

ASN—TYR—ALA—LEU—VAL—ILE—PHE—GLU—
 90    91    92    93    94    95    96    97

MET—VAL—HIS—LEU—LYS—LYS,
     98    99   100   101   102

LYS—ARG—GLY—SER—ARG—LEU—PHE—LEU—
 83    84    85    86    87    88    89

ASN—TYR—ALA—LEU—VAL—ILE—PHE—GLU—
 90    91    92    93    94    95    96    97

MET—VAL—HIS—LEU—LYS—LYS,
     98    99   100   101   102
and

LYS—ARG—GLY—SER—ARG—LEU—LEU—LEU—
 83    84    85    86    87    88    89

ASN—TYR—ALA—LEU—VAL—ILE—PHE—GLU—
 90    91    92    93    94    95    96    97

MET—VAL—HIS—LEU—LYS—LYS.
     98    99   100   101   102

8. A purified or synthetic fragment of the human insulin α subunit, said fragment having a ternary structure as depicted by FIG. 5A or 5B.

* * * * *